(12) United States Patent
Vander Neut et al.

(10) Patent No.: US 10,088,430 B2
(45) Date of Patent: Oct. 2, 2018

(54) SYSTEMS AND METHODS FOR AUTHENTICATING WORKING FLUIDS

(71) Applicant: ExxonMobil Research and Engineering Company, Annandale, NJ (US)

(72) Inventors: Christopher Vander Neut, Mullica Hill, NJ (US); Michael L. Blumenfeld, Haddonfield, NJ (US); Eric B. Senzer, Margate, FL (US); Samuel C. Bainbridge, Houston, TX (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 15/412,099

(22) Filed: Jan. 23, 2017

(65) Prior Publication Data
US 2017/0234804 A1 Aug. 17, 2017

Related U.S. Application Data

(60) Provisional application No. 62/424,763, filed on Nov. 21, 2016, provisional application No. 62/295,269, filed on Feb. 15, 2016.

(51) Int. Cl.
| | |
|---|---|
| *G01N 21/64* | (2006.01) |
| *G01N 21/85* | (2006.01) |
| *G01N 33/22* | (2006.01) |
| *G01N 33/28* | (2006.01) |

(52) U.S. Cl.
CPC ........... *G01N 21/85* (2013.01); *G01N 21/643* (2013.01); *G01N 33/22* (2013.01); *G01N 33/28* (2013.01); *G01N 2021/6439* (2013.01); *G01N 2201/061* (2013.01); *Y10T 436/13* (2015.01); *Y10T 436/21* (2015.01)

(58) Field of Classification Search
CPC ......... G01N 2021/6439; G01N 21/643; G01N 21/85; G01N 2201/061; G01N 33/22; G01N 33/28; Y10T 436/13; Y10T 436/21
USPC ......... 436/56, 60, 164, 172, 139; 422/82.05, 422/82.08, 82.09; 435/4, 6.1
See application file for complete search history.

(56) References Cited

U.S. PATENT DOCUMENTS

| | | | |
|---|---|---|---|
| 3,964,294 A * | 6/1976 | Shair | G01N 30/70 116/200 |
| 5,980,593 A * | 11/1999 | Friswell | C09B 57/02 106/31.15 |
| 6,274,381 B1 | 8/2001 | Pauls et al. | |
| 6,779,505 B2 | 8/2004 | Reischman et al. | |
| 7,157,611 B2 | 1/2007 | Banavali et al. | |
| 7,172,903 B2 | 2/2007 | Schilowitz et al. | |
| 7,241,621 B2 | 7/2007 | Reischman et al. | |
| 7,407,809 B2 | 8/2008 | Reischman et al. | |
| 7,442,936 B2 | 10/2008 | Reischman et al. | |
| 7,689,370 B2 | 3/2010 | Grosser et al. | |
| 7,741,122 B2 | 6/2010 | Reischman | |
| 7,915,048 B2 | 3/2011 | Baxter et al. | |
| 8,354,069 B2 * | 1/2013 | Eastwood | B01D 11/04 205/687 |
| 8,906,698 B2 | 12/2014 | Croud et al. | |
| 2004/0085080 A1 | 5/2004 | Schilowitz et al. | |
| 2004/0248307 A1 | 12/2004 | Grof et al. | |
| 2005/0035755 A1 | 2/2005 | Schilowitz et al. | |
| 2005/0110503 A1 | 5/2005 | Koehler et al. | |
| 2005/0184734 A1 | 8/2005 | Sosnowski et al. | |
| 2005/0241989 A1 * | 11/2005 | Sant | C10M 171/00 208/18 |
| 2006/0118741 A1 | 6/2006 | Ross et al. | |
| 2011/0020940 A1 * | 1/2011 | Knapton | C10L 1/003 436/60 |
| 2011/0229983 A1 * | 9/2011 | Wilkinson | G01N 33/2882 436/501 |
| 2013/0182241 A1 | 7/2013 | Lawandy et al. | |
| 2015/0141264 A1 * | 5/2015 | Jung | C12Q 1/68 506/2 |
| 2015/0300983 A1 * | 10/2015 | Urey | C10L 1/003 204/547 |
| 2016/0242448 A1 | 8/2016 | Ludscher et al. | |

FOREIGN PATENT DOCUMENTS

| | | |
|---|---|---|
| WO | 200431332 A2 | 4/2004 |

OTHER PUBLICATIONS

International Search Report and Written Opinion PCT/US2017/014493 dated Apr. 7, 2017.
International Search Report and Written Opinion PCT/US2017/014495 dated Apr. 7, 2017.

* cited by examiner

*Primary Examiner* — Maureen Wallenhorst
(74) *Attorney, Agent, or Firm* — Anthony G. Boone

(57) ABSTRACT

Systems and methods are provided for authenticating working fluids. The systems and methods include exposing at least a portion of a working fluid containing a UV-reactive chemical marker to light having wavelengths in the range of about 10-400 nm, thereby causing the chemical marker to generate a signal. The signal can be detected via a sensor system and compared to a reference signal that is associated with an authentic working fluid. An output may be generated to indicate whether the working fluid is the authentic working fluid.

5 Claims, 3 Drawing Sheets

SYSTEMS AND METHODS FOR AUTHENTICATING WORKING FLUIDS

CROSS-REFERENCE TO RELATED APPLICATIONS

This application claims the benefit of U.S. Provisional Application No. 62/424,763, filed on Nov. 21, 2016, the entire contents of which are incorporated herein by reference This application also claims the benefit of U.S. Provisional Application No. 62/295,269, filed on Feb. 15, 2016, the entire contents of which are incorporated herein by reference.

FIELD

This invention relates to systems and methods for authenticating working fluids, such as lubricants, oils, coolants, hydraulic fluids, fuels and oil field chemicals, useful in diverse apparatus and mechanical systems.

BACKGROUND

Working fluids are important components of a wide variety of mechanical systems engines). They facilitate functions such as lubricating moving parts, transferring force or energy on the mechanical system, protecting parts against wear, cleanliness, protection of electrical components, or even a combination of these. These fluids may typically contain hydrocarbon base oil formulated with one or more of numerous performance additives selected to enhance one or more performance characteristics.

Unfortunately, counterfeiting of authentic working fluids is a significant problem for working fluid manufacturers. Counterfeit working fluids may be of lower quality than genuine products, and may have inferior properties that can cause harm to the mechanical systems. For example, genuine engine oil may have a freeze point of −10° C. while the counterfeit product may freeze at +1° C., which means that engines utilizing the counterfeit product will suffer from fluid freezing at higher temperatures than anticipated. If consumers are unaware that the fluid is a counterfeit, they may attribute such inferior performance to the genuine product manufacturer, thereby harming brand image.

Additionally, working fluid manufacturers and/or mechanical system manufacturers may wish to offer their customers incentives associated with use of a particular working fluid in a designated mechanical system. In this case, the producers need a way to verify the authenticity of the working fluid that is used.

The industry has developed various methods for authenticating working fluids. Some authentication methods rely on the manual removal of fluid samples from the mechanical system reservoir for testing in a laboratory. However, these approaches are not useful for real-time determination.

U.S. Pat. No. 6,274,381 discloses marking a petroleum hydrocarbon with a visible dye and then exposing it to visible radiation from a suitable light source having wavelengths over the dye's characteristic absorption region. The characteristic absorption is then detected using a light absorption detection system capable of detecting absorption of the petroleum sample in this region to confirm the dye's presence. See Col. 8, lns 59-65. However, one limitation of this approach is that it can only be used with dyes having a wavelength of maximum absorption in the higher portion of the visible spectrum in the region of 500 to 700 nm to avoid interference from inherently strong background absorption of chemical hydrocarbons. See Col. 4, lns 33-41.

The '381 Patent further discloses that markers having virtually no absorbance in the visible portion of the spectrum but absorb and fluoresce in the near infrared region may be used. See Col. 3, lns 4-16. However, '381 Patent further states that such markers are difficult and expensive to make, and there are only a finite number of near infrared absorbing or fluorescing molecules that can serve as silent markers. Col. 3, lns 20-26.

U.S. Patent Pub. No. 2016/0242448 filed on Oct. 8, 2014 entitled "Process for Providing Luminescence In Or From a Food Product" discloses an "edible, safe, comestible compositions containing radiation energy absorbing substances capable of generating luminescence (fluorescence or phosphorescence) upon exposure to an external radiation source." The compositions comprise radiation energy absorbing substances in sufficient amount capable of generating an easily detected (by eye) signal upon exposure to an energy source. The signal generation can be accomplished by using a UV or a visible light source.

Therefore, it is an object of the present disclosure to provide a real-time method for authenticating working fluids that may be employed in situ and overcomes the aforementioned disadvantages.

SUMMARY

In an aspect, a method for authenticating a working fluid is provided. The method includes exposing at least a portion of a working fluid containing a UV-reactive chemical marker to light having wavelengths in the range of about 10-400 nm, thereby causing the chemical marker to generate a signal. The signal can be detected via a sensor system and compared to a reference signal that is associated with an authentic working fluid. An output may be generated to indicate whether the working fluid is the authentic working fluid.

In another aspect, a method for in-situ authentication of a working fluid is provided. The method can include introducing a working fluid containing a UV-reactive chemical marker into a mechanical system. At least a portion of the working fluid is then exposed to a light having wavelengths in the range of about 10-400 nm, thereby causing the chemical marker to generate a signal. The signal may be detected via a sensor system disposed on or within the mechanical system and compared to a reference signal that is associated with an authentic working fluid. An output may be generated to indicate whether the working fluid is the authentic working fluid.

In another aspect, a system for determining whether a working fluid containing a UV-reactive chemical marker is an authentic working fluid is provided. The system may include a control instrument having a reference signal that corresponds to the authentic working fluid and a sensor that is communicatively connected to the control instrument and operable for receiving a signal that is generated from the working fluid upon exposure to UV light. The control system may further be operable for receiving the signal from the sensor and comparing it to a reference signal to determine whether the working fluid is the authentic fluid. The system may further include an output (e.g., display) to indicate whether the working fluid is the authentic working fluid.

DETAILED DESCRIPTION

Described herein are systems and methods for authenticating working fluids such as lubricants, oils, coolants, hydraulic fluids, fuels and oil field chemicals, useful in diverse apparatus and mechanical systems.

The authentic working fluid may contain a UV-reactive chemical marker that can be used to distinguish it from "non-authentic" working fluids.

Suitable UV-reactive chemical markers include any chemical substance that produces a response (e.g., light) on exposure to UV radiation. Examples include dyes, colorants, polyaromatic hydrocarbons, quinones, benziobenasphaltenes, benzothiazoles, derivatives of benzothiazoles, detergents, ionic liquids, metallic nanoparticles, semi-conductor nanoparticles, fluorescent compounds, enzymes, DNA, RNA, polypeptides, fat soluble molecules with specific biological activity, redox-active organometallic complexes and array of molecules with unique molecular weight distributions.

The authentication method includes exposing a working fluid to UV radiation (e.g., light) having wavelengths in the range of about 10-400 nm, or about 100-400 nm, or about 200-400 nm, or about 300-400 nm, or about 350-400 nm, or about 375-400 nm, or about 390-400 nm, or about 395-400 nm.

If the working fluid is authentic, the UV-reactive chemical marker will generate a signal. The signal may be any type of response to the UV radiation, such as fluorescence and/or an RGB color value.

The signal may be detected by any known or hereinafter devised detection system or method. For example, the signal may be visibly detected, or may be detected via one or more sensors. The detection system may be configured to eliminate or reduce interfering signals, such as the IR spectral component of the chemical marker signal. Suitable sensors may include, for example, RGB color value sensors such as those that are commercially available by Adafruit. Additionally or alternatively, the detection system may report the color, temperature and/or the lux of the working fluid.

The signal (if any) generated by working fluid in response to the UV light may then be compared to the known signal (i.e., reference signal) that is associated UV-reactive chemical marker contained in the authentic working fluid. If the two signals match within a specified tolerance, then an output may be generated that indicates that the working fluid is the authentic working fluid. Conversely, if there is no signal match, then an output may be generated to indicate that the working fluid is not the authentic working fluid.

Figure 1:
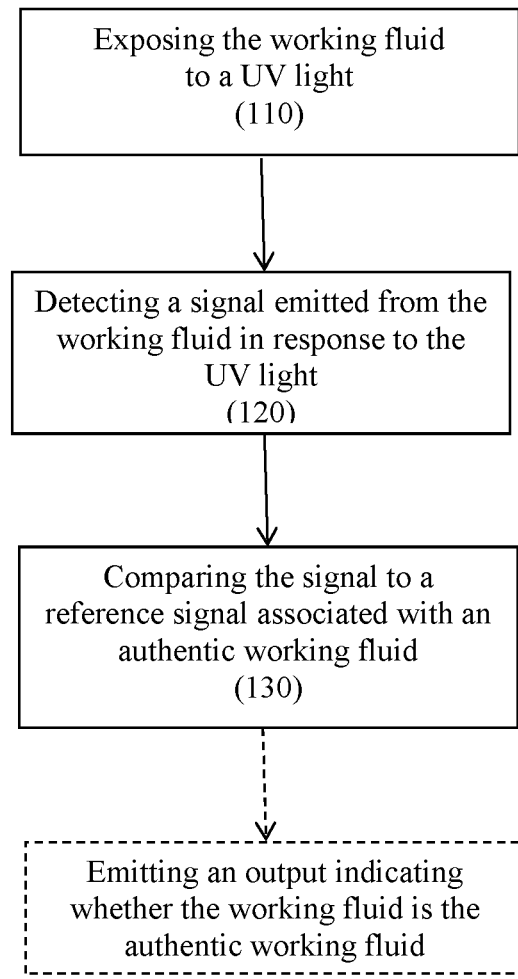
FIG. 1 shows an exemplary method for authenticating working fluids.

With reference to FIG. 1, a method 100 for authentication of a working fluid containing a UV-reactive chemical marker may include: (i) Step 110: exposing at least a portion of the working fluid to light having wavelengths in the range of about 10-400 nm thereby causing the chemical marker to generate a signal; (ii) Step 120: detecting the signal via a sensor system; and (iii) Step 130: comparing the signal to a reference signal that is associated with an authentic working fluid. The method may further include Step 140: generating an output indicating whether the working fluid is the authentic working fluid.

Figure 2:
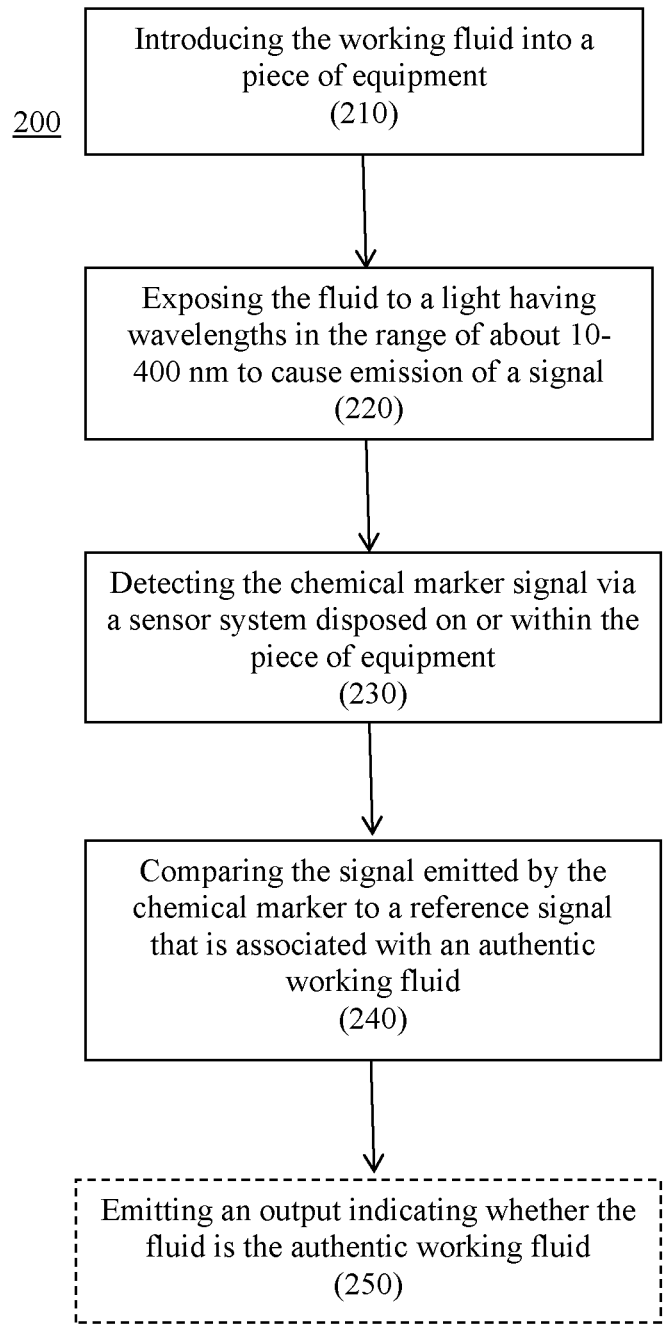
FIG. 2 shows another exemplary method for authenticating working fluids.

With reference to FIG. 2, another method 200 for authenticating a working fluid containing a UV-reactive chemical marker may include: (i) Step 210: introducing the working fluid into a mechanical system; (ii) Step 220: exposing at least a portion of the fluid to a light having wavelengths in the range of about 10-400 nm, thereby causing the chemical marker to generate a signal; (iii) Step 230: detecting the chemical marker signal via a sensor system disposed on or within the mechanical system; and (iv) Step 240: comparing the signal generated by the chemical marker to a reference signal that is associated with an authentic working fluid. The method may further include Step 250: generating an output indicating whether the working fluid is the authentic working fluid.

The detection system may be stand-alone, hand-held or partially or fully located on or within a mechanical system that utilizes a working fluid. For example, the detection system may be located on or within a passenger vehicle or off-road mechanical system. Moreover, the detection system may be partially or fully integrated with other sensor systems and displays used in connection with such mechanical system.

For example, all or part of the detection system may be located in-situ (e.g., on or within one or more of the reservoir, the fill pipe, the filter, the crankcase, the hydraulic piping or the fluid transfer hose of the working mechanical system). For example, a sensor may be located in a fill pipe. As the working fluid is poured into the mechanical device, it flows over the sensor thereby triggering a reading. Moreover, the detection system may be located, configured, and/or insulated so as to reduce or eliminate vibrational and/or other disturbances.

The UV-reactive chemical marker may be present the working fluid in any amount that is detectable by the corresponding detection system or method. The amount of UV-reactive marker in the working fluid may be the minimum amount that will produce a detectable response to UV light. The working fluid may contain, for example, about 1-1000 wppm, or about 1-500 wppm, or about 1-400 wppm, or about 1-300 wppm, or about 1-250 wppm, or about 1-200 wpm, or about 1-150 wppm, or about 1-100 wppm, or about 1-90 wppm, or about 1-80 wppm, or about 1-70 wppm, or about 1-60 wppm, or about 1-50 wppm, or about 1-40 wppm, or about 1-30 wppm, or about 1-20 wppm, or about 1-10 wppm, of the UV-reactive chemical marker. In particular embodiments, the working fluid may contain, for example, about 1-30 wppm, or about 2-30 wppm, or about 3-30 wppm, or about 4-30 wppm, or about 5-30 wppm of the UV-reactive chemical marker.

Once the signal generated from the chemical marker in the working fluid is detected, it may be compared to a reference signal that is associated with an authentic working fluid. If the signals suitably match, an output may be generated to indicate that the working fluid is the authentic fluid. Inversely, if the signals do not suitably match, the system may be configured to generate no output, or may generate an output that indicates that the working fluid is the not authentic fluid.

In some embodiments, the chemical marker in the working fluid and/or the reference signal may be periodically changed (e.g., remotely communicated to the detection system) as a deterrent to would-be counterfeiters.

Any suitable communication system may be used as the output (e.g., verbal, written, electronic, etc.). For example, the output may be displayed (e.g., via a user interface) as an electrical signal, light, or text reading located on or within the piece of working mechanical system. The output may also be transmitted electronically to a remote monitoring location, such as a data bank located in the cloud or a in a centralized control station or any combination thereof.

Additionally or alternatively, the authentication system may include a control instrument that is communicatively connected (e.g., via fiber optic cable or other method) to a UV light source and/or a sensor system. The control system may be located on or within the working mechanical system and may be used to (i) store the reference signal; and/or (ii) activate the UV light source and/or the sensor system.

The authentication system may further include a flow meter located on or within the mechanical system that is communicatively connected to the control instrument and is operable for detecting the flow of working fluid entering the mechanical system. The flow meter may generate and transmit a signal to the control instrument when flow is detected, thereby activating the control system.

The authentication system may further include a user display (e.g., an indicator light or other textual display) located on or within the working mechanical system that is communicatively connected to the control instrument and is operable for indicating to the user whether the working fluid is the authentic working fluid.

Figure 3:
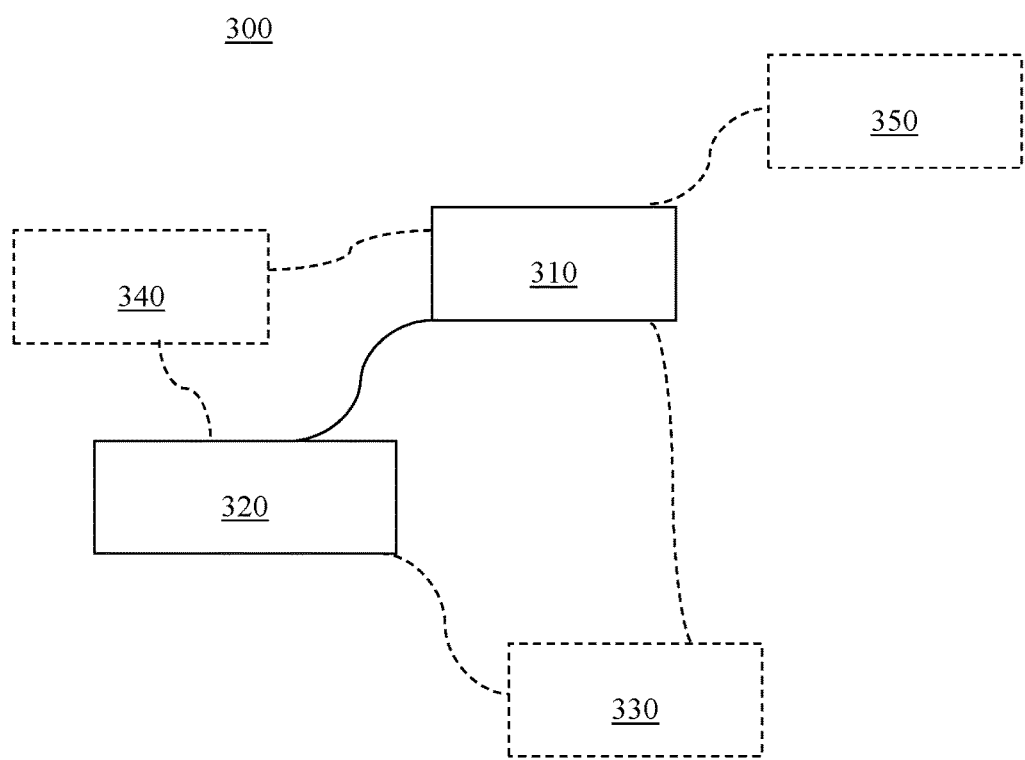
FIG. 3 shows an exemplary system for authenticating working fluids.

With reference to FIG. 3, an authentication system 300 may include (i) a control instrument 310 having a reference signal that corresponds to the authentic working fluid; and (ii) a sensor 320 operable for receiving a signal that is generated from the working fluid upon exposure to UV light, wherein the sensor is communicatively connected to the control instrument. Control instrument 310 may be operable for receiving the signal from sensor 320 and comparing a reference signal to the working fluid signal and generating an output to indicate whether the working fluid is the authentic working fluid. System 300 may further include one or more of (i) a light source 330 that is communicatively connected to one or more of control instrument 310 and/or sensor 320; (ii) a flow meter 340 that is communicatively connected to one or more of control instrument 310 and/or sensor 320; and (iii) an indicator 350 communicatively connected to control instrument 310 to indicate whether the working fluid is the authentic working fluid.

By way of further example with reference to FIG. 3, a working fluid may be introduced into a mechanical system. Flow meter 340 may be located in one or more of the fill pipe, the filter, the reservoir, the crank case, the piping or fluid transfer hose of the mechanical system to detect the flow of the working fluid, which thereby sends a signal to control instrument 310. Control instrument 310 then activates light source 330 to expose the working fluid to UV light and sensor 320 to detect any signal generated from the working fluid in response. Sensor 320 sends the signal to control instrument 310, which compares it to a reference signal. Control instrument 310 activates indicator 350 to indicate whether the working fluid is the authentic working fluid.

ADDITIONAL EMBODIMENTS

Embodiment 1

A method for authentication of a working fluid containing a UV-reactive chemical marker, the method comprising (a) exposing at least a portion of the working fluid to light having wavelengths in the range of about 10-400 nm, thereby causing the chemical marker to generate a signal; (b) detecting the signal via a sensor system; and (c) comparing the signal to a reference signal that is associated with an authentic working fluid.

Embodiment 2

The method of Embodiment 1, further comprising generating an output indicating whether the working fluid is the authentic working fluid.

Embodiment 3

A method for in-situ authentication of a working fluid containing a UV-reactive chemical marker, the method comprising: (a) introducing the working fluid into a mechanical system; (b) exposing at least a portion of the working fluid to a light having wavelengths in the range of about 10-400 nm, thereby causing the chemical marker to generate a signal; (c) detecting the chemical marker signal via a sensor system disposed on or within the mechanical system; and (d) comparing the signal generated by the chemical marker to a reference signal that is associated with an authentic working fluid.

Embodiment 4

The method of Embodiment 3, further comprising generating an output indicating whether the working fluid is the authentic working fluid.

Embodiment 5

The method of Embodiment 3 or 4, wherein the working fluid is selected from a group consisting of a lubricant, an oil, a coolant, an hydraulic fluid, a fuel and an oil field chemical.

Embodiment 6

The method of any of Embodiments 3-5, wherein the chemical marker is selected from a group consisting of a dye, a colorant, a polyaromatic hydrocarbon, asphaltene, detergent, ionic liquid, metallic nanoparticle, semi-conductor nanoparticle, fluorescent compound, enzyme, DNA, RNA, polypeptide, fat soluble molecule with specific biological activity, redox-active organometallic complex and array of molecules with unique molecular weight distributions.

Embodiment 7

The method of any of Embodiments 3-6, wherein the chemical marker is a quinone and the signal generated by the chemical marker is fluorescence.

Embodiment 8

The method of any of Embodiments 3-7, wherein the signal generated by the chemical marker is a RGB color value.

Embodiment 9

The method of any of Embodiments 3-8, wherein the sensor at least partially minimizes the IR spectral component of the chemical marker signal.

Embodiment 10

The method of any of Embodiments 3-9, wherein the sensor system is located on or within one or more of the reservoir, the fill pipe, the filter, the crankcase, the hydraulic piping or the fluid transfer hose of the system.

Embodiment 11

The method of any of Embodiments 3-10, wherein at least a portion of the sensor system is insulated from one or more of vibrational and environmental disturbances.

Embodiment 12

The method of any of Embodiments 3-11, wherein generating an output comprises one or more of: (i) displaying the output on an user interface on the mechanical system; and (ii) transmitting the output to a remote location.

Embodiment 13

The method of any of Embodiments 3-12, herein the reference signal is remotely communicated to the sensor system and the reference signal is periodically changed.

Embodiment 14

A system for determining whether a working fluid containing a UV-reactive chemical marker is an authentic working fluid, the system comprising (i) a control instrument having a reference signal that corresponds to the authentic working fluid; and (ii) a sensor operable for receiving a signal that is generated from the working fluid upon exposure to UV light, wherein the sensor is communicatively connected to the control instrument, wherein the control instrument is operable for receiving the signal from the sensor and comparing the reference signal to the working fluid signal and generating an output to indicate whether the working fluid is the authentic working fluid.

Embodiment 15

The Embodiment of embodiment 14, wherein the working fluid is selected from a group consisting of a lubricant, an oil, a hydraulic fluid, a fuel and an oil field chemical.

Embodiment 16

The Embodiment of embodiment 14 or 15, wherein the working fluid is disposed on or within a mechanical system, and the sensor and the control instrument are mounted on or within the mechanical system.

Embodiment 17

The Embodiment of any of embodiment 14-16, wherein the sensor is located on or within one of the reservoir, the fill pipe, and the filter of the mechanical system.

Embodiment 18

The Embodiment of any of embodiment 14-17, wherein the sensor and the light source are each connected to the sensor via fiber optic cable.

Embodiment 19

The Embodiment of any of embodiment 14-18, wherein the signal generated by the working fluid is a RGB color value.

Embodiment 20

The Embodiment of any of embodiment 14-19, further comprising a light source communicatively connected to the control instrument, wherein the light source is operable to deliver to the working fluid a UV light having wavelengths in the range of about 10-400 nm.

Embodiment 21

The Embodiment of any of embodiment 14-20 further comprising a flow meter disposed on or within the mechanical system, wherein the flow meter is communicatively connected to the control instrument and is operable to detect the flow of working fluid entering the mechanical system and generate a signal to the control instrument when flow is detected.

Embodiment 22

The Embodiment of embodiment 20, wherein the control instrument activates the light source and the sensor in response to the signal received from the flow meter.

Embodiment 23

The Embodiment of any of embodiment 14-22, further comprising an indicator located on or within the mechanical system and is communicatively connected to the control instrument, and wherein the indicator indicates whether the working fluid is the authentic working fluid.

Although the present invention has been described in terms of specific embodiments, it is not so limited. Suitable alterations/modifications for operation under specific conditions should be apparent to those skilled in the art. It is therefore intended that the following claims be interpreted as covering all such alterations/modifications as fall within the true spirit/scope of the invention.

All numerical values within the detailed description and the claims herein are modified by "about" or "approximately" the indicated value, and take into account experimental error and variations that would be expected by a person having ordinary skill in the art.

The invention claimed is:
1. A method for in-situ authentication of a working fluid containing a UV-reactive chemical marker, the method comprising:
   introducing the working fluid into a mechanical system wherein the working fluid is selected from a group consisting of a lubricant, an oil, a coolant, an hydraulic fluid, a fuel and an oil field chemical;
   exposing at least a portion of the working fluid to a light having wavelengths in a range of about 10-400 nm, thereby causing the chemical marker to generate a signal;
   detecting the chemical marker signal via a sensor system disposed on or within the mechanical system; and
   comparing the signal generated by the chemical marker to a reference signal that is associated with an authentic working fluid;

further comprising generating an output indicating whether the working fluid is the authentic working fluid wherein the chemical marker is a quinone and the signal generated by the chemical marker is fluorescence.

2. A method for in-situ authentication of a working fluid containing a UV-reactive chemical marker, the method comprising:
   introducing the working fluid into a mechanical system wherein the working fluid is selected from a group consisting of a lubricant, an oil, a coolant, an hydraulic fluid, a fuel and an oil field chemical;
   exposing at least a portion of the working fluid to a light having wavelengths in a range of about 10-400 nm, thereby causing the chemical marker to generate a signal;
   detecting the chemical marker signal via a sensor system disposed on or within the mechanical system; and
   comparing the signal generated by the chemical marker to a reference signal that is associated with an authentic working fluid
   wherein the signal generated by the chemical marker is a RGB color value.

3. The method of claim 2, wherein the chemical marker is selected from a group consisting of a dye, a colorant, a polyaromatic hydrocarbon, asphaltene, quinone, detergent, ionic liquid, metallic nanoparticle, semi-conductor nanoparticle, fluorescent compound, enzyme, DNA, RNA, polypeptide, redox-active organometallic complex and array of molecules with unique molecular weight distributions.

4. A system for determining whether a working fluid containing a UV-reactive chemical marker is an authentic working fluid, the system comprising:
   a control instrument having a reference signal that corresponds to the authentic working fluid;
   a sensor operable for receiving a signal that is generated from the chemical marker in the working fluid upon exposure to UV light, wherein the sensor is communicatively connected to the control instrument wherein the working fluid is selected from a group consisting of a lubricant, an oil, a hydraulic fluid, a fuel and an oil field chemical,
   wherein the control instrument is operable for receiving the signal from the sensor and comparing the reference signal to the working fluid signal and generating an output to indicate whether the working fluid is the authentic working fluid wherein the chemical marker is selected from a group consisting of a dye, a colorant, a polyaromatic hydrocarbon, asphaltene, quinone, detergent, ionic liquid, metallic nanoparticle, semi-conductor nanoparticle, fluorescent compound, enzyme, DNA, RNA, polypeptide, redox-active organometallic complex and array of molecules with unique molecular weight distributions and wherein the signal generated by the chemical marker in the working fluid is a RGB color value.

5. A system for determining whether a working fluid containing a UV-reactive chemical marker is an authentic working fluid, the system comprising:
   a control instrument having a reference signal that corresponds to the authentic working fluid;
   a sensor operable for receiving a signal that is generated from the chemical marker in the working fluid upon exposure to UV light, wherein the sensor is communicatively connected to the control instrument wherein the working fluid is selected from a group consisting of a lubricant, an oil, a hydraulic fluid, a fuel and an oil field chemical,
   wherein the control instrument is operable for receiving the signal from the sensor and comparing the reference signal to the working fluid signal and generating an output to indicate whether the working fluid is the authentic working fluid wherein the chemical marker is a quinone and the signal generated by the chemical marker is fluorescence.

* * * * *